United States Patent [19]

Nishimura et al.

[11] Patent Number: 5,327,773
[45] Date of Patent: Jul. 12, 1994

[54] METHOD AND APPARATUS FOR MEASURING STEAM DENSITY BY NEUTRON METHOD

[75] Inventors: Tatsuo Nishimura, Tokyo; Michio Katou, Saitama; Yasuyuki Hashi, Tokyo, all of Japan

[73] Assignee: Japan National Oil Corporation, Tokyo, Japan

[21] Appl. No.: 15,465

[22] Filed: Feb. 9, 1993

[30] Foreign Application Priority Data

Mar. 10, 1992 [JP] Japan ................. 4-051613

[51] Int. Cl.5 ................................. G01N 31/00
[52] U.S. Cl. ................... 73/30.01; 73/29.01
[58] Field of Search ............. 73/29.01, 30.01; 376/245, 159

[56] References Cited

U.S. PATENT DOCUMENTS

| | | | |
|---|---|---|---|
| 4,645,635 | 2/1987 | Yuen et al. | 376/245 |
| 4,832,503 | 5/1989 | Dowling et al. | 73/29.01 |
| 4,849,988 | 7/1989 | Chien | 73/29.01 |
| 5,094,103 | 3/1992 | Wicks, III et al. | 73/29.01 |

*Primary Examiner*—Hezron E. Williams
*Assistant Examiner*—Valerie D. Francies
*Attorney, Agent, or Firm*—Brooks Haidt Haffner & Delahunty

[57] ABSTRACT

A method and an apparatus capable of measuring the density of steam within a steam pipe even in limited environmental conditions such as in a steam injection well. A vessel which accommodates therein first and second neutron detectors disposed in mutual longitudinal alignment with a neutron source interposed therebetween and in which the second detector is covered with a neutron shield capable of absorbing thermal neutrons while allowing epithermal neutrons to penetrate therethrough is inserted into the steam pipe together with a thermal neutron shielding sheet completely encircling the vessel. From the neutrons which were emitted from the neutron source and passed out and back through the neutron shield and the steam region, those epithermal neutrons which have not undergone transformation to thermal neutrons within the steam region are detected by both the first and second detectors, while the thermal neutrons resulting from the transformation are detected by the first detector only. The steam density is determined on the basis of a cadmium ratio derived from the counts of the two detectors.

7 Claims, 9 Drawing Sheets

PRIOR ART

METHOD AND APPARATUS FOR MEASURING STEAM DENSITY BY NEUTRON METHOD

BACKGROUND OF THE INVENTION

1. Field of the Invention

The present invention relates to a method and an apparatus for measuring the density of steam within a steam pipe which is provided in a plant and through which steam is caused to flow. The present invention will hereinafter be described in relation to the density measurement of down-hole steam in a steam injection well in the petroleum industry as a typical industrial field to which the invention can be applied. It should however be understood that the present invention is not restricted to such specific field but can find application in steam density measurement in any plant equipped with a steam pipe which prohibits or hinders the measurement of steam density from the exterior.

2. Description of the prior Art

Although no apparatus has yet been developed for measuring the density of down-hole steam in steam injection wells in the petroleum industry, there have been proposed several approaches for measurement of the steam density within steam pipes leading to some injection wells from boilers in the enhanced oil recovery equipment installed on the ground for carrying out the steam injection process.

Figure 8:
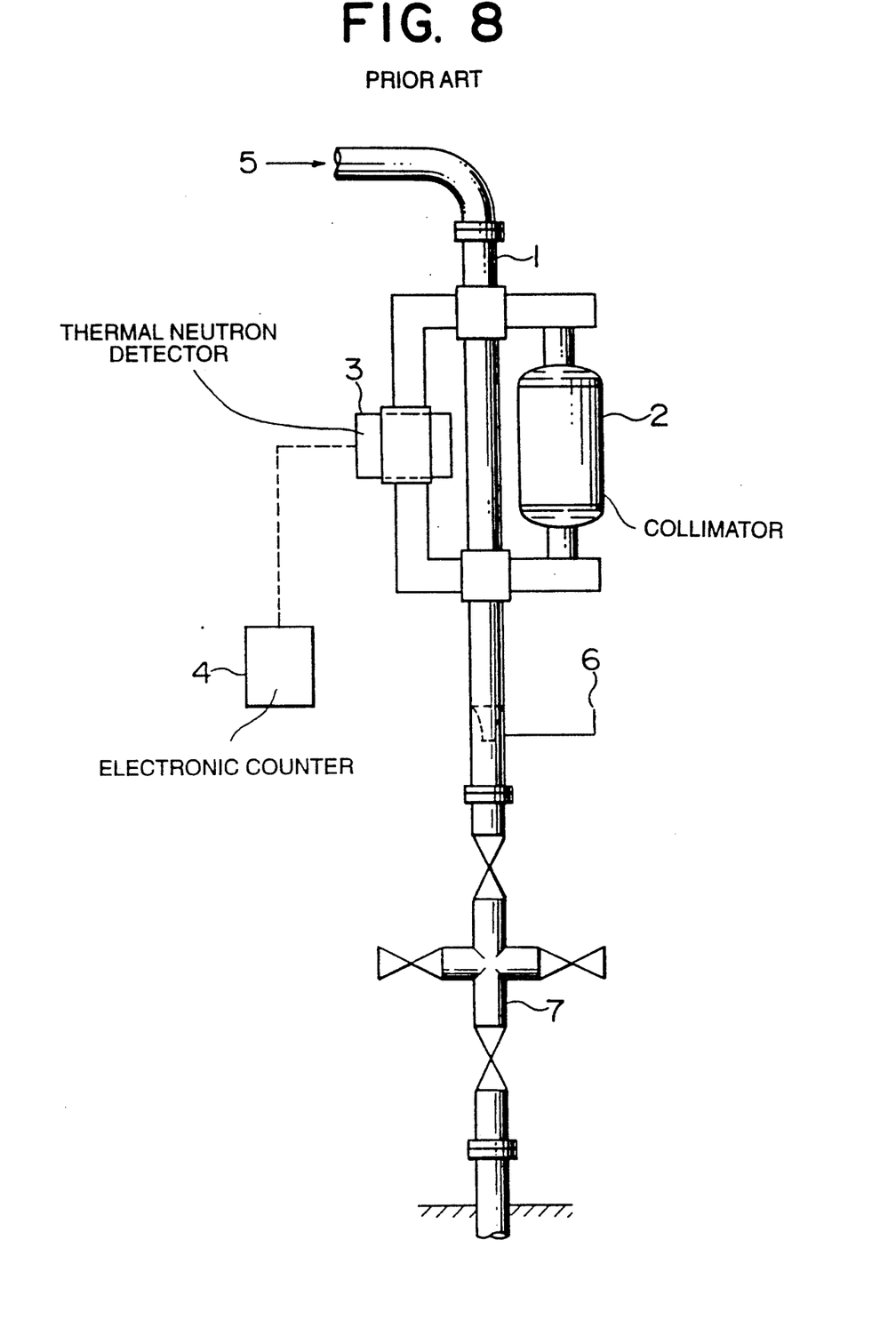
FIG. 8 is a schematic elevational view showing a steam density measuring apparatus known heretofore.
Figure 9:
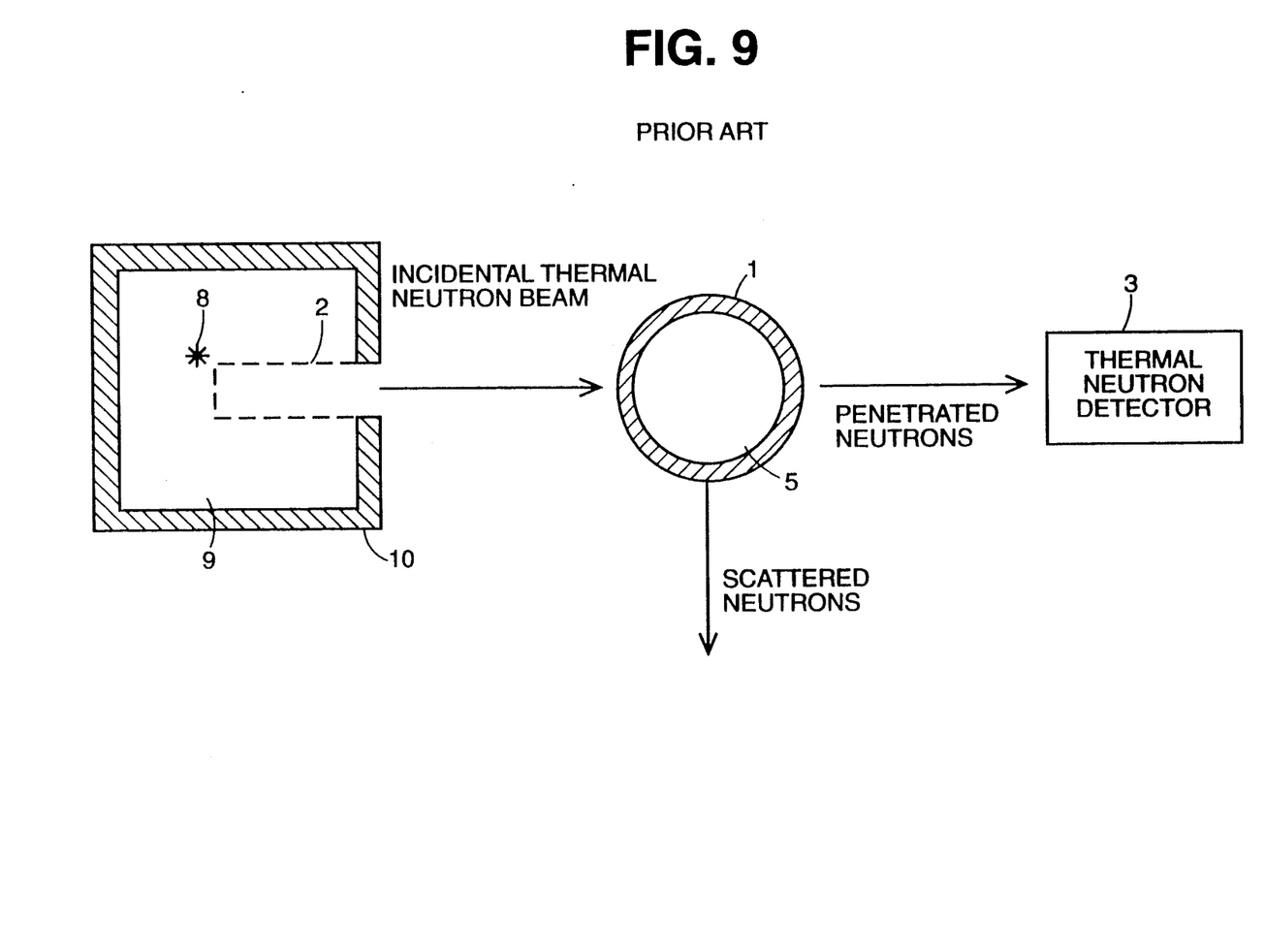
FIG. 9 is a view for illustrating the principle underlying the steam density measuring apparatus shown in FIG. 8.

FIGS. 8 and 9 of the accompanying drawings show, by way of example, a steam density measuring apparatus known heretofore. In these figures, reference numeral 1 denotes a steam pipe, and numeral 2 denotes a collimator for obtaining a neutron beam, which collimator is constituted by a neutron source 8 accommodated within a neutron shield 10 and a neutron moderator 9. Further, reference numeral 3 denotes a thermal neutron detector, 4 denotes an electronic counter instrument, and 5 designates a flow of steam. The steam 5 flows through a flow nozzle 6 disposed within the steam pipe 1 to reach the top end of the steam injection well 7. In this steam density measuring apparatus, there is made use of a direct relation existing between the decay of thermal neutrons in the wet steam and mean density and void fraction of the wet steam.

More specifically, the wet steam flows through the steam pipe 1 under a significantly high pressure, about 2,500 psig. The collimator 2 incorporating the neutron source 8 of a radioisotope is disposed at one side of the steam pipe 1 while the thermal neutron detector is disposed in diametrical opposition to the collimator 2 relative to the steam pipe 1. The thermal neutron detector exhibits a high sensitivity to thermal and epithermal neutrons for detecting any thermal/epithermal neutrons emitted from the neutron source 8 that are transmitted or penetrate through the steam pipe 1. The output signal of the thermal neutron detector 3 is supplied to the electronic counter instrument 4 to be processed to thereby generate a signal having a magnitude that is in proportion to the count value of the thermal/epithermal neutrons indicating the density of steam flowing through the steam pipe 1. In this manner, the density of steam confined within the steam pipe can be measured.

The steam density measuring apparatus of the structure shown in FIGS. 8 and 9 is certainly effective in such applications where there is a space available for allowing the collimator 2 including the neutron moderator to be disposed in opposition to the thermal neutron detector 3 around the steam pipe 1. On the other hand, as a steam density measuring apparatus designed for use where the space for installation of the collimator and the detector mentioned above can not be secured around the steam pipe 1, there has also been proposed a structure such as the steam density measuring apparatus in which all the components thereof are located only at one side of the steam pipe 1, as shown in FIG. 10 of the accompanying drawings.

Figure 10:
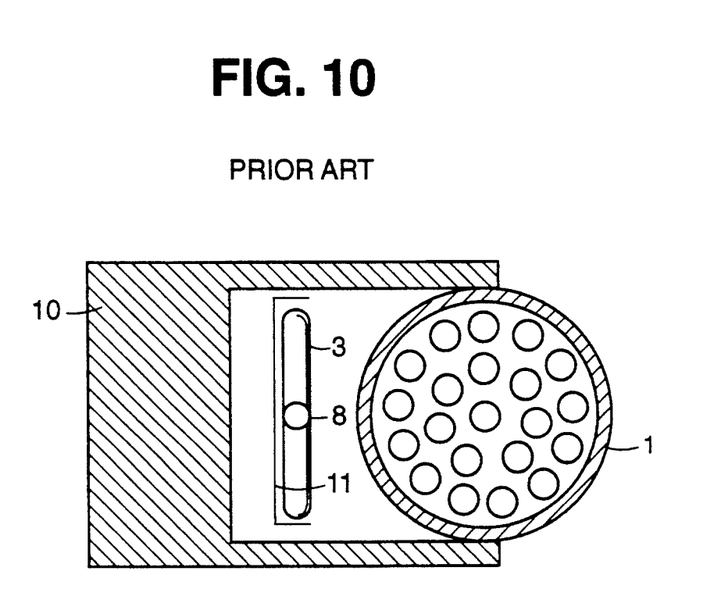
FIG. 10 is a sectional view also showing another example of a prior art steam density measuring apparatus.

Referring to FIG. 10, the steam density measuring apparatus illustrated is so implemented as to detect those neutrons emitted from a Cf-252 type neutron source having a mean energy of 2.3 MeV that have been back scattered in the wet steam by making use of the linear relation existing between the scattering of neutrons within the wet steam and the mean density and void fraction of the wet steam. More specifically, in FIG. 10, wet steam flows within and through a steam pipe 1 under high pressure (e.g., 2,500 psig). A neutron shielding member 10 is disposed at one side of the steam pipe 1, wherein the neutral shielding member 10 encases therein a Cf-252 type neutron source 8, a cadmium plate 11 and a BF-3 type neutron detector (termed BF-3 detector hereafter) 3. The BF-3 detector 3 has an enhanced sensitivity for thermal/epithermal neutrons and is capable of detecting those thermal/epithermal neutrons which are back scattered from the steam pipe 1. The neutron shielding member 10 serves to shield the neutrons emitted from the Cf-252 type neutron source for protecting those persons who are working in the vicinity against exposure to radiation. On the other hand, the cadmium plate 11 functions to absorb those thermal neutrons which experience moderating and scattering and would otherwise penetrate through the neutron shielding member 10 (and become noise sources). The signal obtained from the BF-3 detector 3 can then be processed in the same manner as described above in conjunction with the steam density measuring apparatus shown in FIGS. 8 and 9.

As is apparent from the foregoing, the steam density measuring apparatuses known heretofore are designed to measure the density of steam within a steam pipe in a plant installed above ground and require in any case a space which allows the measuring apparatus to be disposed at least at one side of the steam pipe. Thus, it is impossible to use the prior art steam density measuring apparatus in a physically limited environment such as a steam injection well where the measurement of the density of down-hole steam is needed.

SUMMARY OF THE INVENTION

Accordingly, it is an object of the present invention to provide a method and an apparatus which are capable of measuring with accuracy and reliability the density of steam flowing within a steam pipe even in a spatially restricted environment such as encountered, for example, in a steam injection well.

In view of the above and other objects which will become apparent as description proceeds, there is provided according to an aspect of the present invention a method of measuring the density of steam within a steam pipe by a method utilizing neutrons. The method comprises the steps of providing a vessel accommodating first and second neutron detectors disposed in mutual longitudinal alignment with a neutron source being interposed therebetween. In the longitudinal alignment the second neutron detector is covered with a neutron shield capable of absorbing thermal neutrons while allowing epithermal neutrons to penetrate or pass therethrough. The vessel mentioned above is inserted into the steam pipe together with a thermal neutron shielding sheet completely covering the vessel with a gap relative to the vessel, the gap serving as a steam flow path. Both neutron detectors detect neutrons which were emitted from the neutron source and transmitted through the neutron shield and which have again passed through the neutron shield in the opposite direction to again reach the steam region. Epithermal neutrons which have not undergone transformation to thermal neutrons within the steam region are detected by means of both the first and second neutron detectors while thermal neutrons resulting from the transformation are detected by means of the first neutron detector only. The density of the steam is determined on the basis of a cadmium ratio (representing the probability of the epithermal neutrons being transformed to the thermal neutrons) on the basis of the counts of the two neutron detectors.

Further provided according to a second aspect of the invention is an apparatus for measuring the density of steam within a steam pipe by a neutron method, which apparatus comprises a hollow vessel defining therein a space, a neutron source disposed within the space of the vessel, neutron detecting means including first and second neutron detectors disposed in a longitudinal array within the space with the neutron source being interposed between the first and the second neutron detectors in the longitudinal direction, wherein the second neutron detector is covered with a neutron shield of cadmium that absorbs thermal neutrons while allowing epithermal neutrons to be transmitted therethrough, signal receiving/density computing means for receiving signals from the first and the second neutron detectors constituting the neutron detecting means to thereby compute the density of the steam on the basis of a cadmium ratio determined on the basis of the signals available from the outputs of the neutron detectors, and a thermal neutron shield of a cylindrical shape circumferentially covering the vessel with an annular gap between the thermal neutron shield and an outer surface of the vessel.

The fast neutrons emitting from the neutron source penetrate through the vessel accommodating the neutron source, the first and second neutron detectors and others as well as the steam region. In that case, the fast neutrons emitting from the neutron source penetrate through the first and second neutron detectors disposed at both sides of the neutron source. However, since the detection sensitivities of these neutron detectors to the fast neutrons are low, (about three decades less than with thermal neutrons) contribution of the fast neutrons to the counting rates of concern can be neglected. The neutrons reach the steam region after having penetrated through the vessel. However, these fast neutrons can not be slowed down to the thermal/epithermal levels for which the neutron detectors exhibit high sensitivity but penetrate to the regions located outside of the steam region.

In the example where the present invention is applied to the measurement of the density of down-hole steam of a steam injection well, the fast neutrons reach a brine layer, cementing layer and/or the formation where the fast neutrons are slowed down to thermal/epithermal neutrons. A part of these moderated neutrons can penetrate deeper into the formation to be absorbed therein, while another part of these neutrons will again reach the steam region due to back-scattering. In that case, in the path of penetrating through the neutron shield disposed outside of the container, a major part of the thermal neutrons is absorbed by the neutron shield, resulting in that substantially only the epithermal neutrons can reach the steam region. These surviving epithermal neutrons are prone to be transformed to thermal neutrons within the steam region. In this conjunction, it is noted that a linear relation exists between the probability of the epithermal neutrons being transformed to thermal neutrons and the density of steam.

The epithermal neutrons which are not transformed to thermal neutrons within the steam region are detected by the first and second neutron detectors. However, the thermal neutrons resulting from the above-mentioned transformation are detected only by the first neutron detector, because the second neutron detector is enclosed by a thermal neutron absorbing material such as cadmium which absorbs the thermal neutrons to thereby keep them from being detected by the second neutron detector.

BRIEF DESCRIPTION OF THE DRAWINGS

The objects, features and attendant advantages of the present invention will be better understood upon reading the following description of preferred embodiments of the steam density measuring method and apparatus taken in conjunction with the accompanying drawings, in which like reference numerals denote like or equivalent parts and in which.

DESCRIPTION OF THE PREFERRED EMBODIMENTS

Figure 1:
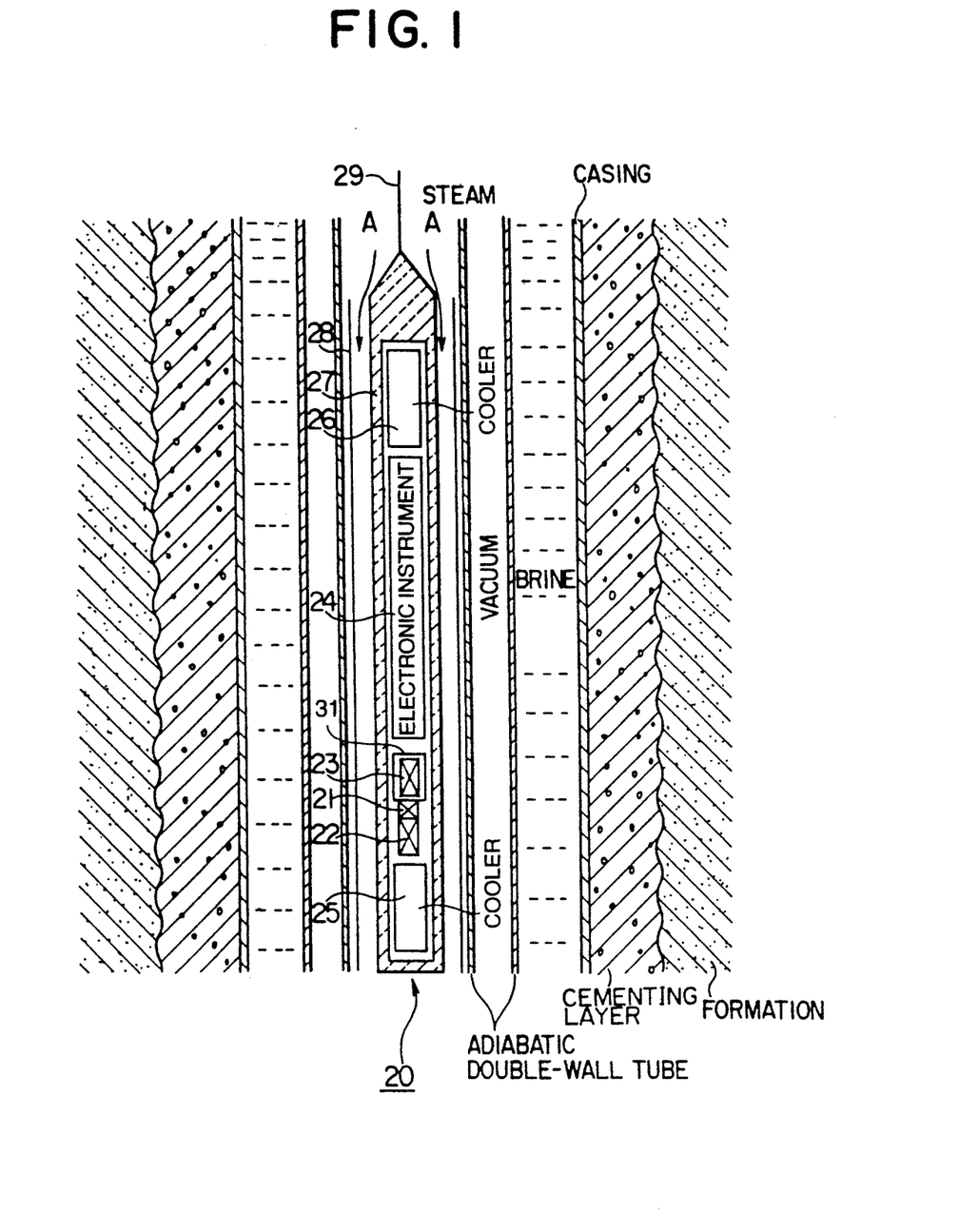
FIG. 1 is a sectional view showing an apparatus for carrying out a steam density measuring method according to the present invention.
Figure 2:
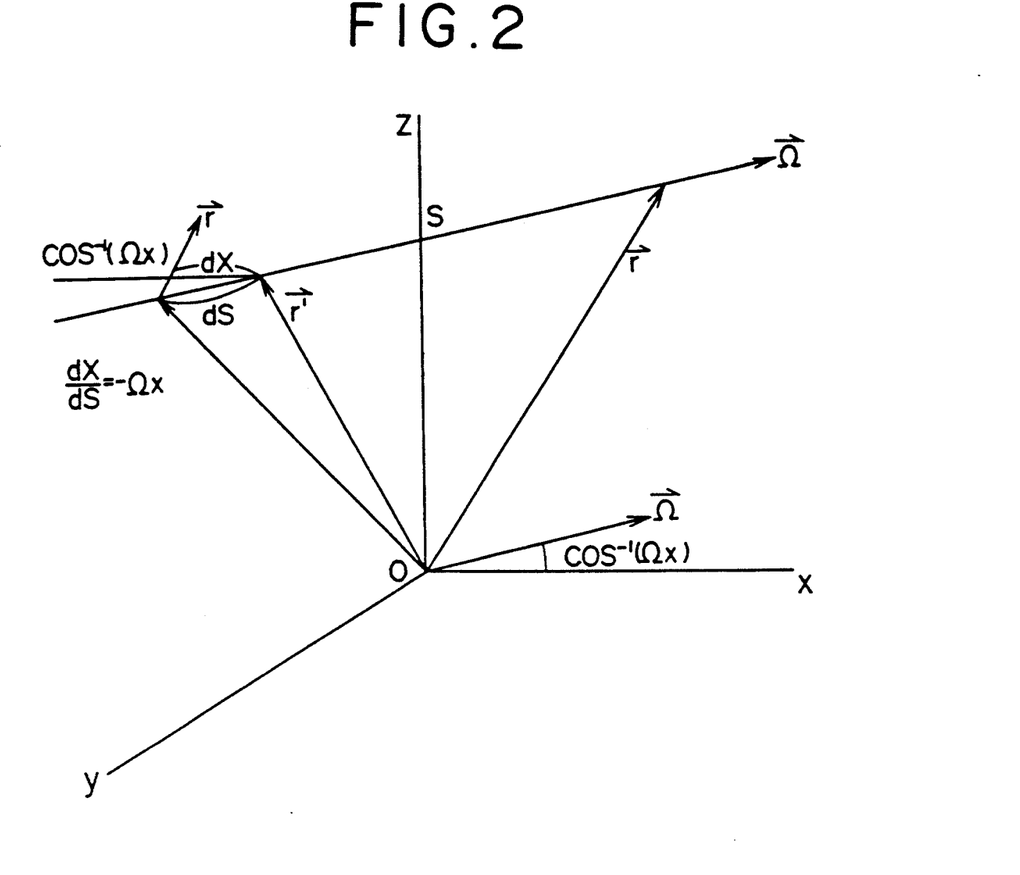
FIG. 2 is view for illustrating the principle underlying the invention.

FIG. 1 is a sectional view showing an apparatus for carrying out a steam density measuring method according to an example of the present invention in the state in which the apparatus has been inserted into a steam injection well. Referring to the figure, a steam density measuring apparatus 20 includes an adiabatic vessel 27 of an elongated cylindrical form (which may have a vacuum bottle type structure or be a container equipped with a cooler), wherein there are accommodated within the adiabatic vessel 27 a neutron source 21, a first neutron detector 22, a second neutron detector 23 which has the same configuration, size and detection sensitivity as the first neutron detector 22 and is wrapped with a cadmium shield 31, the second neutron detector 23 being disposed above the first neutron detector 22, an electronic instrument 24 schematically shown as disposed above the second neutron detector 23, and lower and upper coolers 25 and 26. The electronic instrument 24 connected to the neutron detectors 22 and 23 may be constituted by a signal detector, a signal processor and a power supply source although they are omitted from the illustration.

Mounted externally around the adiabatic vessel 27 with a predetermined distance therefrom is a cylindrical neutron shield 28 which is constituted by a sheet of cadmium having both surfaces covered with stainless steel sheets, respectively. Connected to a top end of the adiabatic vessel 27 in a manner as shown in FIG. 1 is a wire line 29 which is coupled to a winding machine (not shown) installed above ground and which serves for transmitting the signal output from the neutron detectors 22 and 23 to an electronic system installed above ground via the electronic apparatus 24, for supplying electric power to the latter and for positioning the sonde type adiabatic vessel 27 within the injection well upon insertion thereof.

As can be seen in FIG. 1, the injection well is constituted by a casing buried in the formation so as to coaxially surround an adiabatic double-wall tube with a layer of brine being interposed between the casing and the tube, wherein an annular space defined by the double walls of the adiabatic tube is maintained under vacuum. Further, cement is injected from the ground surface to form a cementing layer surrounding the casing. The adiabatic vessel 27 is suspended within the inner space of the double-wall tube by means of the wire line 29. Arrows A indicate the flow of steam or water vapor.

Next, the description will turn to operation of the steam density measuring apparatus described above. Fast neutrons emanating from the neutron source 21 travel through the adiabatic vessel 27, the steam flow A and the vacuum space of the double-wall tube to reach the brine layer, cementing layer and the formation. In that case, the fast neutrons emitted from the neutron source 21 also penetrate through the neutron detectors 22 and 23 disposed below and above the neutron source 21, respectively, but the detection sensitivity of the neutron detectors 22 and 23 is lower than that for fast neutrons, and the contribution of these neutrons to the counting rate is negligible. After having penetrated through the adiabatic vessel 27, the neutrons reach the steam flow area. However, because the energy of neutrons is high (about 2.3 MeV), they penetrate to regions located outside of the steam region without slowing down to the thermal/epithermal levels to which the neutron detectors mentioned above exhibit high detection sensitivity.

On the other hand, the fast neutrons reaching the brine layer, cementing layer or the formation are slowed down to the thermal/epithermal levels because of the high hydrogen content of these layers due to the presence of water. Although a part of the moderated neutrons penetrate deeper into the formation to be absorbed thereby, another part of the neutrons will return to the vacuum region to again reach the steam flow region. In that case, a major part of the thermal neutrons are absorbed by the cylindrical neutron shield 28 disposed around the adiabatic vessel 27 in the path of the penetrating neutrons, as a result of which substantially only the epithermal neutrons can reach the steam flow region. These surviving epithermal neutrons are slowing down to thermal neutrons in the steam flow region. In this context, it is to be pointed out that a linear relationship exists between the probability of transformation of the epithermal neutrons to thermal neutrons in the steam region and the density of steam.

The epithermal neutrons not transformed to thermal neutrons in the steam region are detected by both neutron detectors 22 and 23, while the thermal neutrons are detected only by the neutron detector 22. This is because the neutron detector 23 is enwrapped by a thermal neutron absorbing material such as cadmium which absorbs the thermal neutrons to thereby keep the neutron detector 23 from detecting the thermal neutrons.

Some of the problems encountered in measuring the steam density in the environment described above are the transition of brine from a saturated water state to a saturated-vapor state and eventually to an empty state as a function of time from the injection of steam, and the dispersion or nonuniformity in water content throughout the cementing layer and the formation. Additionally, there are uncertainties such as non-uniformity in the thickness of the cementing layer, the differences in formations from one steam injection well to another, etc. These uncertainties in environmental conditions will result in too great a variation in the counts of neutrons detected by the neutron detectors 22 and 23 to determine steam density on the basis of a linear relation between the neutron counts and steam densities.

Under the circumstances, the present invention teaches that these uncertainties in environmental conditions can be eliminated by measuring a cadmium ratio which is defined as follows:

$$\text{Cadmium ratio} = (A - B)/A$$

where
A represents the count of neutrons detected by the neutron detector 22 during a predetermined period of measurement (i.e., count of thermal neutrons+epithermal neutrons), and
B represents the count of neutrons detected by the neutron detector 23 during a predetermined period (i.e., the count of epithermal neutrons).

The cadmium ratio will next be analyzed from the theoretical standpoint. Behavior of radiation in a material or substance can be expressed by solving the Boltzmann transport equation which macroscopically describes motions of a particle (neutron in this case) within a substance (or medium). The concept of the cadmium ratio mentioned above can be qualitatively derived from the physical concept represented by the transport equation.

First, the Boltzmann transport equation in the steady state is given by the following expression (1):

$$\Omega \cdot \nabla \phi(\vec{r}, E, \vec{\Omega}) + \Sigma_t(\vec{r}, E) \phi(\vec{r}, E, \vec{\Omega}) = \int dE' \int d\Omega' \Sigma_s (\vec{r}, E' \rightarrow E, \vec{\Omega}' \rightarrow \vec{\Omega}) \phi(\vec{r}, E', \vec{\Omega}') + S(\vec{r}, E, \vec{\Omega}) \quad (1)$$

The above equation can be transformed to an integral form as follows:

$$\psi(\vec{r}, E) = \int \chi(\vec{r}, E) \, T(\vec{r}' \rightarrow \vec{r}, E) \, d\vec{r}' \quad (2)$$

$$\chi(\vec{r}, E) = \int \psi(\vec{r}, E) \, C(E \rightarrow E, \vec{r}) \, dE + S(\vec{r}, E) \quad (3)$$

where $\psi\,(\vec{r},\,E),\,\chi\,(\vec{r},\,E)$: collision densities,
$T\,(\vec{r}' \rightarrow \vec{r},\,E)$: transport kernel,
$C\,(E' \rightarrow E,\,\vec{r})$: collision kernel, and
$S\,(\vec{r},\,E)$: radiation source term.

The transport kernel $T\,(\vec{r}' \rightarrow \vec{r},\,E)$ can be given by the following expression (4):

$$T(\vec{r}' \rightarrow \vec{r}, E) = \Sigma t(\vec{r}, E) \exp\left[-\int_0^W \Sigma t(\vec{r}' + \vec{S}\vec{\Omega}, E) dS\right] \quad (4)$$

where $W = \vec{\Omega} \cdot (\vec{r} - \vec{r}')$.

Further, the collision kernel $C\,(E' \rightarrow E,\,\vec{r})$ can be expressed as follows:

$$C(E' \rightarrow E, \vec{r}) = P \cdot C(E' \rightarrow E, \vec{r}) \quad (5)$$

where $$P = \frac{\Sigma s(\vec{r}, E')}{\Sigma t(\vec{r}, E')} \quad (6)$$

$$C(E' \rightarrow E, \vec{r}) = \frac{1}{4\pi} f(E' \rightarrow E, \vec{r})$$

In the expressions mentioned above,
$\Sigma t\,(\vec{r},\,E')$: total cross section at particle position $\vec{r}$ of energy E,
$\vec{\phi}$: unit vector representing the traveling direction of a particle of energy E (refer to FIG. 3),
$\vec{r} - \vec{r}'$: vector parallel to $\Omega$ and satisfying $\vec{\Omega} \cdot (\vec{r} - \vec{r}') \geq 0$ for all $\vec{r}$,
$\Sigma s(\vec{r},\,E)$: scattering cross section at particle position $\vec{r}$ of energy E, and
$f(E' \rightarrow E,\,\vec{r})$: probability distribution function of particle energy E' scattering to E at the particle position $\vec{r}$.

The collision densities $\psi\,(\vec{r},\,E)$ and $\chi\,(\vec{r},\,E)$ can be given in terms of sums of numbers of collisions n of particles as follows:

$$\psi(\vec{r}, E) = \sum_{n=1}^{\infty} \psi_n(\vec{r}, E) \quad (7)$$

$$\chi(\vec{r}, E) = \sum_{n=1}^{\infty} \chi_n(\vec{r}, E) \quad (8)$$

where
$\psi_n$: collision density after $(n-1)$ collisions, and
$\chi_n$: collision density making appearance after n collisions (where n equal to "0" indicates emission of particle from radiation source).

By using the expressions (7) and (8), the relations mentioned below can be obtained:

$$\chi_0(\vec{r}, E) = S(\vec{r}, E) \quad (9)$$

$$\chi_n(\vec{r}, E) = \int \psi_n(\vec{r}, E') C(E' \rightarrow E, \vec{r}) dE' \ (n=1, 2 \ldots) \quad (10)$$

$$\psi_{n+1}(\vec{r}, E) = \int \chi_n(\vec{r}', E) T(\vec{r}' \rightarrow \vec{r}, E) d\vec{r}' \ (n=0, 1, 2 \ldots) \quad (11)$$

Figure 3:
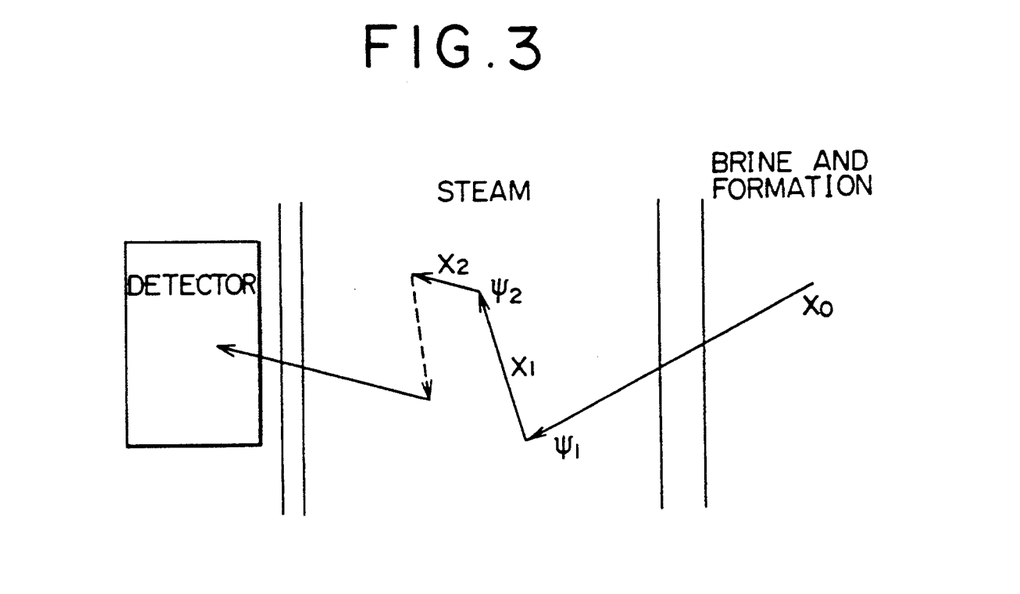
FIG. 3 is a schematic view for illustrating environmental conditions of a steam injection well to which the present invention can be applied.

Here, the environmental conditions of the steam injection well will be considered (refer to FIG. 3). Assuming that the contribution of those neutrons which impinge upon the detectors directly or by way of the steam phase from the neutron source can be neglected, the expressions (7) and (8) will be valid for neutrons which have reached the brine layer and the formation from the neutron source and scattered within these layers to be returned to the steam flow region.

In this case, since the neutron source is put aside from consideration, the expression (9) can be replaced by the following expression (12):

$$\chi_0(\vec{r}, E) = \int \psi_{FOR}(\vec{r}, E') C_{FOR}(E' \rightarrow E, \vec{r}) dE' \text{ (where } E > 0.414 \text{ eV)} \quad (12)$$

In the above expression (12), $\psi_{FOR}\,(\vec{r},\,E')$ represents the collision densities before the last collisions within the brine layer and the formation. The reason for setting the energy of $\chi_0\,(\vec{r},\,E)$ higher than 0.414 eV is based on the presumption that energy after the last collisions in the brine layer and the formation becomes lower than 0.414 eV, whereby the particles returned to the steam flow region are absorbed by the cadmium shield and thus the relevant component can be previously put aside from consideration.

Next, for the purpose of defining the cadmium ratio on the basis of the counting rate, the collision kernel is defined by the following expression (13) for the case where energy E after collision in the steam region is lower than 0.414 eV for discriminating the collision kernel from that given by the general expression (3)

$$C'(E' \rightarrow E, \vec{r}) \text{ (where } E > 0.414 \text{ eV)} \quad (13)$$

In case the energy E after collision is not postulated to be higher than 0.414 eV, the general expression (3) is used.

Similarly, the collision density $\chi_n\,(\vec{r},\,E)$ is defined by the following expression (14) for discrimination from the collision density given by the expression (10). Namely, $$\chi_n'(\vec{r}, E) = \int \psi_n(\vec{r}, E) C'(E' \rightarrow E, \vec{r}) dE' \ (E > 0.414 \text{ eV}) \quad (14)$$

In case the energy E after collision is not limited to the level higher than 0.414 eV, the expression (10) mentioned previously applies valid. It can however be understood that $\chi_0'\,(\vec{r},\,E)$ is same as that given by the expression (12) and thus $\chi_0'\,(\vec{r},\,E)$ is equal to $\chi_0\,(\vec{r},\,E)$.

Further, representing by $\Sigma\,R_{HE-3}\,(E,\,\vec{R})$ a reaction cross section of a filled gas contributing to the counting rate of the detector, the transported nuclei represented by $T'\,(\vec{r}' \rightarrow \vec{R},\,E)$ which reach the detector after the last collision in the steam region can be given by $$T'(\vec{r}' \rightarrow \vec{R}, E) = \Sigma \vec{R}_{HE-3}(E,\vec{R}) \exp\left[-\int_0^W \Sigma t(\vec{r}' + \vec{S}\vec{\Omega}, E) dS\right] \quad (15)$$

where $W = \vec{\Omega} \cdot (\vec{R} - \vec{r}')$.

Thus, the cadmium ratio contributing ultimately to the counting rate can be defined as follows:

$$A = \int_{VD} d\vec{r} \int_0^\infty dE \int_{VS} d\vec{R} \left[\sum_{n=1}^{\infty} \chi_n(\vec{r}, E) T'(\vec{r} \rightarrow \vec{R}, E)\right] +$$

$$B = \int_{VD} d\vec{r} \int_0^\infty dE \int_{VR} d\vec{R} [\chi_0(\vec{r}, E) T'(\vec{r} \rightarrow \vec{R}, E)]$$

-continued $$\int_{VD} d\vec{r}' \int_{0.414eV} dE \int_{VS} d\vec{R} \left[ \sum_{n=1}^{\infty} \chi_n'(\vec{r}',E) T(\vec{r}' \to \vec{R},E) \right] +$$

$$\int_{VD} d\vec{r}' \int_{0.414eV} dE \int_{VR} d\vec{R} [\chi_0(\vec{r}',E) T(\vec{r}' \to \vec{R},E)]$$

and hence, cadmium ratio $= (A - B)/A$     (16)

where

VS: volume of steam phase region,
VD: volume of detector region, and
VR: volume of brine and the formation.

As can be seen from the expression (16), since the second terms as well as the succeeding terms in the infinite series of $\chi_n(\vec{r}, E)$ and $\chi_n'(\vec{r}, E)$ are determined on the basis of the first terms (defined by the expression (12)) in accordance with the expressions (10) and (11), the first term which is a common divisor of the numerator and the denominator of the expression (16) can be eliminated.

As is apparent from the above, the cadmium ratio derived from the counting rates of the detectors is independent of the densities of collisions occurring within the brine and the formation and can be determined on the basis of the collision kernel and the transport kernel. Among others, it is the collision kernel that has the main influence on the cadmium ratio. As can be understood from the expression (16), sensitivity of the cadmium ratio becomes higher as the difference between C' (E'→E, $\vec{r}$) determining $\chi_n'(\vec{r}', E)$ in the numerator and C (E'→E, $\vec{r}$) determining $\chi_n(\vec{r}', E)$ in the denominator increases.

In other words, it can reasonably be said that the sensitivity of the cadmium ratio is enhanced for a given change in the steam density because of the remarkable difference between the probability of the neutron energy becoming lower than 0.414 eV and the probability of the neutron energy becoming higher than 0.414 eV after scattering in dependence on hydrogen contained in the steam.

Accordingly, although the collision density of neutrons generated within the brine layer and the formation and traveling toward the steam region changes depending on the density of the brine, the type of the formation, and the hydrogen content of the cementing layer as well as the thickness thereof, the cadmium ratio will remain unvaried so long as the density of steam within the injection well is constant with the condition that the profile of soft energy spectrum shifted to the low energy range above the lower limit of 0.414 eV and below about $10^5$ eV, is relatively constant. In reality, the same result has been obtained in respect to the energy spectrum in the brine layer and the formation from simulative analyses actually carried out by changing the density of brine, type of formation and thickness of the cement layer. A typical neutron energy spectrum in these regions is illustrated in FIG. 4.

Figure 4:
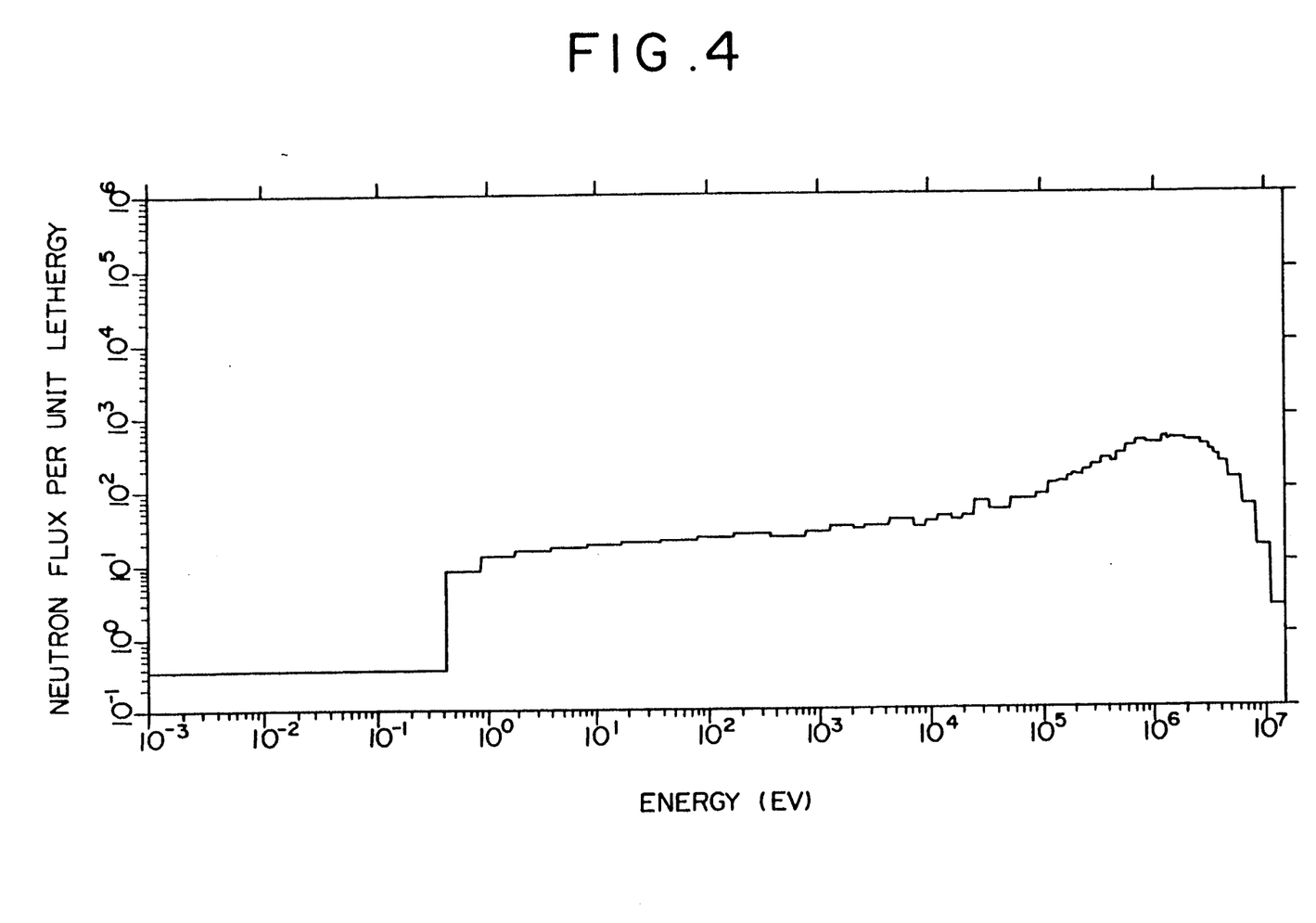
FIG. 4 is a view showing typically a neutron energy spectrum in a brine layer and a formation.

For realizing the condition that the profile of energy spectrum in the brine layer, formation, etc. is relatively constant, i.e., as shown in FIG. 4, it is necessary that the fast neutrons reaching the brine layer, formation, etc. from the neutron source are so moderated as to increase the portion of neutrons below about $10^5$ eV. To this end, it is satisfied since the brine and the formation contain water which is an excellent moderator of the fast neutrons. In this context, it is believed that no practical problem will arise even if the adiabatic double-wall tube becomes empty, because the cementing layer and the formation contain water or moisture.

Figure 5:
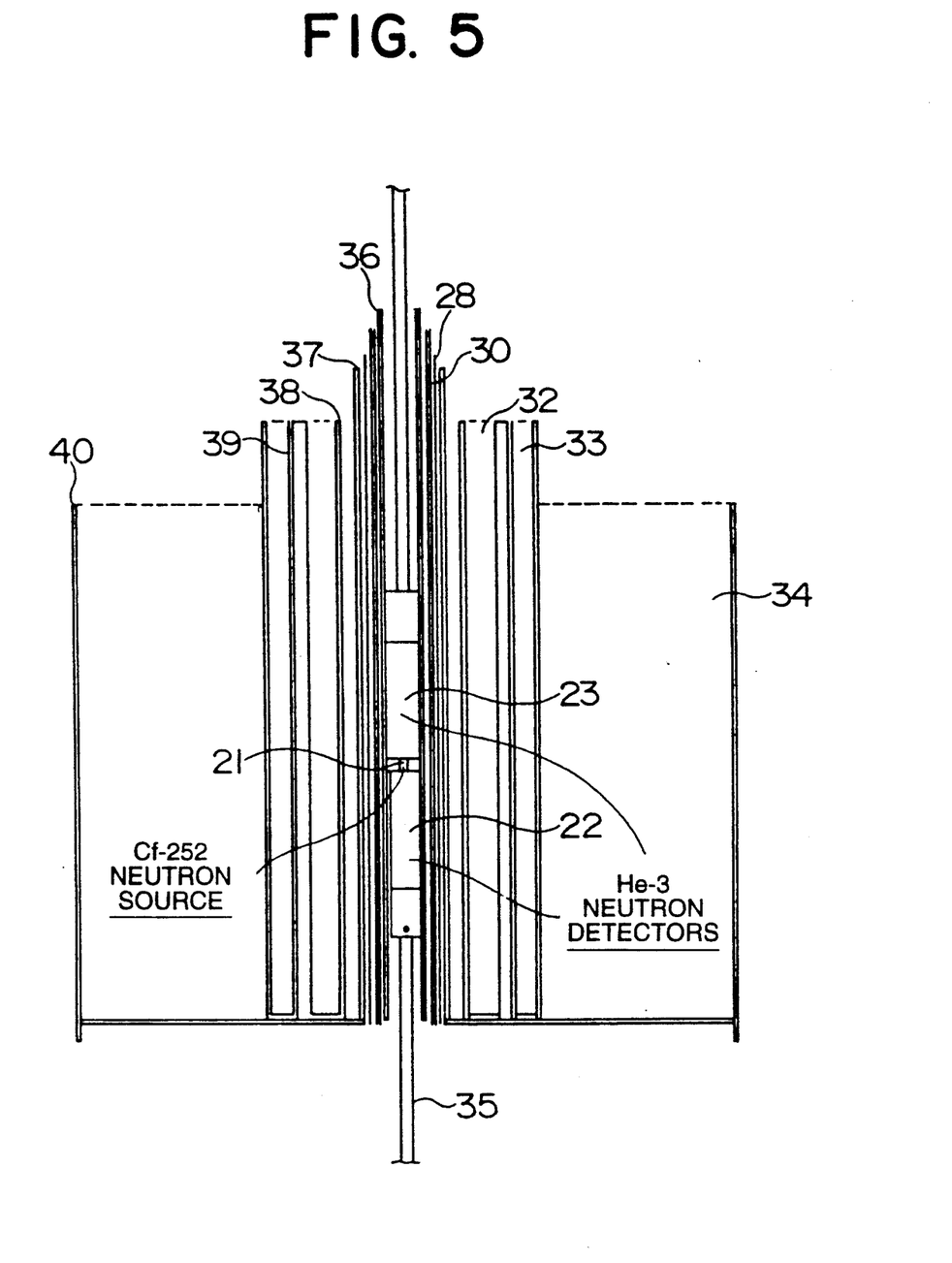
FIG. 5 is a schematic diagram illustrating a mock-up for steam density measurement which simulates a steam injection well and environmental conditions thereof.

It has experimentally been established that the measurement of the steam density within the injection well can be carried out regardless of possible variations in the environmental condition, when the steam density measuring method according to the invention based on the cadmium ratio is employed, as is apparent from the theoretical analysis of the cadmium ratio discussed above. FIG. 5 shows an experimental system which simulates a steam injection well and environmental conditions thereof, wherein there are accommodated within a sonde type adiabatic vessel according to the invention a neutron detecting system comprising a combination of a neutron source and a pair of neutron detectors in the manner described hereinbefore.

More specifically, in FIG. 5, reference numeral 21 denotes a Cf-252 type neutron source, 22 denotes a He-3 type neutron detector, 23 denotes a neutron detector having the same configuration, size and sensitivity as the neutron detector 22 and enclosed by a cadmium layer, 28 denotes a cylindrical neutron shield (sheet of cadmium), and 30 denotes a region wound with polyethylene sheet as a substitute for steam, wherein change in the steam density can be simulated by changing the volume of the polyethylene sheet. In the case of the system shown in FIG. 1, a vacuum region is provided. However, the experimental system shown in FIG. 5 is filled with air.

Although numeral 32 denotes a brine layer, by filling this region with water or air, it is possible to simulate the phase changes of brine. Numeral 33 denotes polyethylene pebbles used in substitution for water contained in the cementing layer. Finally, reference numeral 34 denotes a mass of calcium carbonate which simulates limestone constituting the formation.

Further, reference numeral 35 denotes a power supply/signal transmission cable for the He-3 type neutron detector, 36 denotes a mock-up of the adiabatic vessel, 37 denotes a mock-up of the inner wall of the adiabatic double-wall tube, 38 denotes a mock-up outer wall of the adiabatic double-wall tube, 39 denotes a container housing the polyethylene pebbles, and 40 denotes a container for accommodating calcium carbonate simulating the formation.

The experiment was carried out for six cases in total by changing the density of polyethylene used in place of steam to three different values for each case where the brine layer was filled with water (i.e., at a water density of 1.0 g/cm$^3$) and where the brine layer was empty (i.e., at a water density of 0.0 g/cm$^3$). The density of polyethylene was converted into steam density based on the atomic weight ratios of water and polyethlene in order for the hydrogen content to be equivalent to steam and the density in terms of steam density at the three values of 0.0 g/cm$^3$, 0.082 g/cm$^3$ and 0.222 g/cm$^3$.

Figure 6:
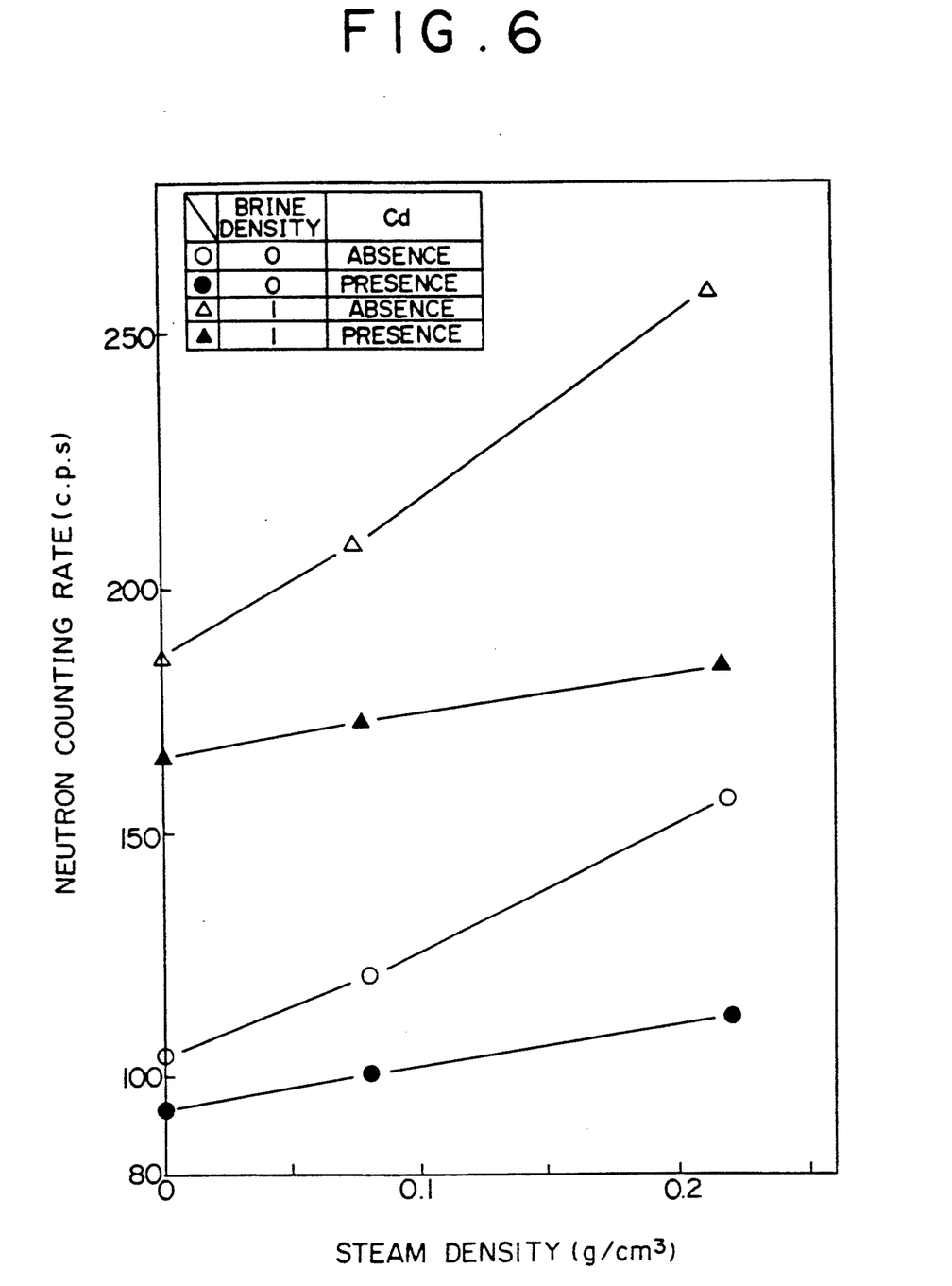
FIG. 6 is a view showing relations existing between steam density and neutron counting rate.

For the six cases mentioned above, the counting rates detected by the He-3 type neutron detector 22 and the neutron detector 23 wound with the cadmium wrapper are shown in Table 1. Relations between these counting rates and the steam densities are graphically illustrated in FIG. 6. As can be seen in FIG. 6, the counting rates of the individual detectors vary by a factor of about two in the cases where the brine layer is filled with water or evacuated, respectively.

TABLE 1

| WATER DENSITY OF CEMENTING LAYER (gH₂O)/cm³) | WATER DENSITY OF BRINE LAYER (gH₂O)/cm³) | STEAM DENSITY (gH₂O)/cm³) | He-3 DETECTOR Cd SHIELDING | NEUTRON COUNTING RATE(*) (cps) | CADMIUM RATIO (**) |
|---|---|---|---|---|---|
| 0.779 (polyethylene pebbles) | 0.0 (air) | 0.0 (air) | absence | 104.3 | 0.111 |
| | | | presence | 92.7 | |
| | | 0.082 (polyethylene sheet) | absence | 121.8 | 0.169 |
| | | | presence | 100.6 | |
| | | 0.222 (polyethylene sheet) | absence | 157.4 | 0.288 |
| | | | presence | 112.1 | |
| | 1.0 (water) | 0.0 | absence | 185.9 | 0.111 |
| | | | presence | 165.3 | |
| | | 0.082 | absence | 208.6 | 0.172 |
| | | | presence | 172.8 | |
| | | 0.222 | absence | 258.8 | 0.287 |
| | | | presence | 184.4 | |

Figure 7:
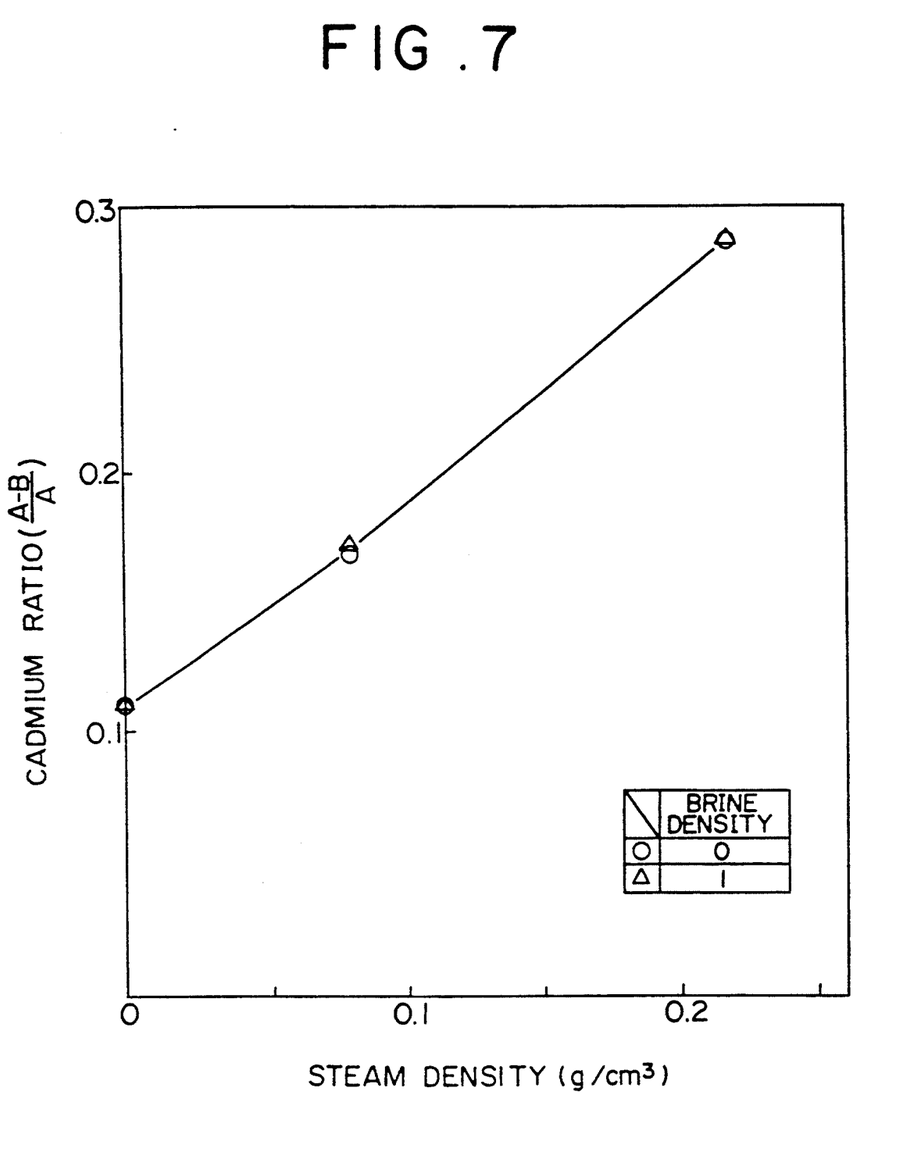
FIG. 7 is a view showing relations existing between steam density and cadmium ratio.

(*)duration of neutron counting rate measurement was 300 sec.
(**)cadmium ratio = (A − B)/A The cadmium ratio was computed on the basis of the counting rates of the neutron detectors and are shown in Table 1 as well, while relations between the cadmium ratio and the steam density is shown in FIG. 7. As will be seen from Table 1 and FIG. 7, the cadmium ratio scarcely undergoes any appreciable changes even when the brine layer changes from the state filled with water to the empty state.

An experimental system or model such as the one shown in FIG. 5 is provided above ground as the standard for calibration. By inserting the sonde type steam density measuring apparatus according to the invention into a steam injection well while determining a calibration curve representing the relation between the cadmium ratio and the steam density such as shown in FIG. 7, it is possible to measure the down-hole steam density of a steam injection well of a temperature higher than 100° C. In this conjunction, it should however be added that the method according to the invention can equally find application not only in the steam density measurement of steam injection wells but also in plants utilizing steam as well as in the steam density measurement of geothermal wells and the detection of water spring during winze digging.

As will be apparent from the foregoing, it is possible to measure steam density even within a restricted space according to the present invention by virtue of the vessel accommodating therein first and second neutron detectors in a longitudinal array with a neutron source interposed therebetween, wherein the vessel is externally enclosed with a neutron shield capable of absorbing thermal neutrons while allowing the epithermal neutrons to penetrate therethough.

Further, according to the present invention, the vessel is inserted into a steam tube, and among those neutrons which were emitted from the neutron source, penetrated through the neutron shield and then repenetrated the neutron shield in the opposite direction to reach the steam region again, those epithermal neutrons which have not undergone transformation to thermal neutrons within the steam region are detected through cooperation of the first and second neutron detectors while the thermal neutrons resulting from the transformation are detected only by the first neutron detector. The density of the steam is determined on the basis of the cadmium ratio derived from the counts of the first and the second neutron detectors. Thus, there can be provided a steam density measuring method and an apparatus therefor which are substantially insusceptible to uncertainties in the environmental condition in which the apparatus is used.

We claim:

1. A method of measuring the density of steam within a steam pipe by a neutron method, comprising the steps of:

providing a vessel accommodating first and second neutron detectors disposed in mutual longitudinal alignment with a neutron source interposed therebetween, said second neutron detector being covered with a neutron shield capable of absorbing thermal neutrons while passing epithermal neutrons therethrough;

inserting said vessel into said steam pipe together with a thermal neutron shielding sheet wholly encircling said vessel with a gap therebetween, said gap serving as a steam flow path;

detecting with both of said neutron detectors the epithermal neutrons that return after traveling out and back from said neutron source through said steam flow path, and detecting only with said first neutron detector also those returning neutrons that have undergone transformation to thermal neutrons; and determining the density of the steam on the basis of a cadmium ratio derived from the response of said two neutron detectors.

2. An apparatus for measuring the density of steam within a steam pipe by a neutron method, comprising:

a hollow vessel defining therein a space;

a neutron source disposed within said space of said vessel;

neutron detecting means including first and second neutron detectors disposed in a longitudinal array within said space with said neutron source interposed between said first and second neutron detectors in the longitudinal direction, said second neutron detector being covered with a first thermal neutron shield of cadmium which absorbs thermal neutrons while allowing epithermal neutrons to penetrate therethrough;

signal receiving/density computing means for receiving signals from said first and second neutron detectors for computing the density of the steam on the basis of a cadmium ratio determined from said signals; and a second thermal neutron shield of cylindrical shape circumferentially encircling said vessel with an annular gap between said second thermal neutron shield and a peripheral surface of said vessel.

3. A steam density measuring apparatus according to claim 2, wherein said vessel is formed of an adiabatic material.

4. A steam density measuring apparatus according to claim 2, wherein said second thermal neutron shield is composed of a sheet of cadmium having both surfaces covered with a sheet of stainless steel.

5. A steam density measuring apparatus according to claim 2, wherein said signal receiving/density computing means includes an electronic instrument accommodated within said vessel and wire means electrically connected to said electronic instrument and mechanically connected to said vessel for supporting the same.

6. A steam density measuring apparatus according to claim 5, wherein a cooler is disposed within said vessel.

7. A steam density measuring apparatus according to claim 6, wherein said cooler is disposed adjacent to said electronic instrument.

* * * * *